United States Patent [19]
Luzzi

[11] Patent Number: 5,574,163
[45] Date of Patent: Nov. 12, 1996

[54] PROCESS FOR THE PREPARATION OF N-OXYL HINDERED AMINE ESTERS

[75] Inventor: John J. Luzzi, Carmel, N.Y.

[73] Assignee: Ciba-Geigy Corporation, Tarrytown, N.Y.

[21] Appl. No.: 298,898

[22] Filed: Aug. 31, 1994

[51] Int. Cl.⁶ .................................................. C07D 211/46
[52] U.S. Cl. .................................................. 546/242
[58] Field of Search ...................................... 546/242

[56] References Cited

U.S. PATENT DOCUMENTS

| | | | |
|---|---|---|---|
| 4,665,185 | 5/1987 | Winter et al. | 546/184 |
| 5,218,116 | 6/1993 | Neri et al. | 544/106 |

FOREIGN PATENT DOCUMENTS

| | | | |
|---|---|---|---|
| 0488403 | 6/1992 | European Pat. Off. | |
| 1168556 | 7/1985 | U.S.S.R. | |

OTHER PUBLICATIONS

Chem. Abst. 117:29206a (1993).
Chem. Abst. 120:7714a (1994).
Chem. Abst. 119:49937a (1993).
Chem. Abst. 112:119591q (1990).
Izu. Akad. Nauk. SSSR, Ser. Khim, 11, 2578 (1981).
Free Radical Res. Comm. 9 (3–6), 379 (1990).
C.A. 109:92734n (1988).
Chem. Papers 42(2) 243–248 (1988).
C.A. 96:84950c (1982).

*Primary Examiner*—C. Warren Ivy
*Assistant Examiner*—Raymond Covington
*Attorney, Agent, or Firm*—Luther A. R. Hall

[57] ABSTRACT

When a tetraalkyl orthotitanate transesterification catalyst is used in the preparation of N-oxyl hindered amine esters, the N-oxyl compound is obtained in excellent yield and purity when moderate temperatures (90°–130° C.) and an aliphatic hydrocarbon solvent are used. The N-oxyl compounds are light stabilizers and also inhibitors for preventing the premature polymerization of ethylenically unsaturated monomers.

23 Claims, No Drawings

5,574,163

PROCESS FOR THE PREPARATION OF N-OXYL HINDERED AMINE ESTERS

This invention pertains to an improved process for the preparation of N-oxyl derivatives of hindered mines, particularly hindered amine esters. These N-oxyl derivatives are light stabilizers and also effective inhibitors for preventing the premature polymerization of ethylenically unsaturated monomers.

BACKGROUND OF THE INVENTION

The instant N-oxyl compounds can be prepared in a number of ways. One method is described in U.S. Pat. No. 4,665,185 where a hindered amine having an N—H moiety is oxidized with a hydroperoxide in the presence of an appropriate metal carbonyl, oxide or alkoxide catalyst, such a tert-butyl hydroperoxide in the presence of molybdenum trioxide catalyst.

The oxidation of a hindered amine with hydrogen peroxide in the presence of sodium tungstate catalyst is reported by V. Kaliska et al., Chem. Pap., 42 (2), 243-8 (1988)[Chem. Abst. 109, 92734n (1988)]. The use of ultrasound facilitates the reaction when the hindered amine has a fatty acid group at the 4-position of the piperidine ring.

The preparation of the instant N-oxyl compounds has also been described by the transesterification of the lower alkyl ester of a carboxylic acid with the 1-oxyl hindered amine alcohol as taught by I. Drăgutan, Free Radical Res. Comm. 9 (3–6), 379 (1990) and by V. D. Sholle et al., Izv. Akad. Nauk. SSSR, Ser. Khim, 11, 2578 (1981)[Chem. Abst. 96, 84950c (1982)] using sodium methoxide or sodium ethylate as catalyst. It is noted that these catalysts including lithium amide cause severe decomposition and the formation of oxidation-reduction by-products in many of the reactions causing little of the desired N-oxyl ester product to form.

U.S. Pat. No. 5,218,116 teaches that hindered amines can be oxidized to their N-oxyl derivatives with hydrogen peroxide in the presence of a titanium catalyst which is a titanium silicalite or synthetic zeolite. EP 574,667 A1 teaches that divalent metal catalysts are useful for the same purpose.

Russian (SU) patent No. 1,168,556 describes the preparation of 1-oxyl-2,2,6,6-tetramethylpiperidin-yl esters of carboxylic acids by reaction of the corresponding 4-hydroxy compound with a lower alkyl ester of a mono- or di-carboxylic acid at 125°–140° C. in the presence of a tetraalkyl orthotitanate transesterification catalyst in xylene. The yields are reported to vary from 51 to 84%. The patent further states that, when the reaction is run at a temperature below 125° C., the yields obtained are considerably lower.

In actuality, due to the reactive nature of the N-oxyl group, using the conditions described in the Russian reference, namely in xylene at 140° C., the desired N-oxyl product is produced in low yield accompanied by a host of various by-products.

Although the Russian reference genetically describes a method for making such N-oxyl ester products, discrete chemically significant improvements in said process have resulted in an improved process for making the instant N-oxyl ester products in higher yields and with excellent purity at lower temperature and with more benign solvent systems.

DETAIL DISCLOSURE

The instant improved process for the preparation of an N-oxyl compound of formula I

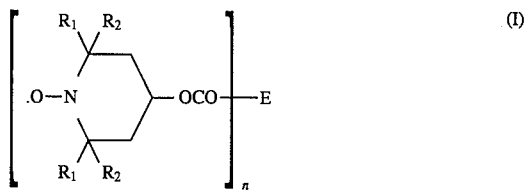

wherein
n is 1,2,3 or 4,
$R_1$ and $R_2$ are independently methyl or ethyl, or $R_1$ and $R_2$ together are pentamethylene,
when n is 1, E is alkyl of 1 to 19 carbon atoms, alkenyl of 2 to 17 carbon atoms, phenyl or said phenyl substituted by 1 to 3 alkyl of 1 to 4 carbon atoms,
when n is 2, E is a direct bond, alkylene of 2 to 12 carbon atoms, o-phenylene, m-phenylene or p-phenylene,
when n is 3, E is alkanetriyl of 3 to 7 carbon atoms, 1,2,4-benzenetriyl or 1,3,5-benzenetriyl, and
when n is 4, E is alkanetetrayl of 4 to 8 carbon atoms or 1,2,4,5-benzenetetrayl,
by the reaction of essentially n equivalents of

with one equivalent of

E-[COOT]

where T is alkyl of 1 to 4 carbon atoms, and $R_1$, $R_2$ n and E are as described above, in the presence of a tetraalkyl orthotitanate or a trialkoxy titanium chloride transesterification catalyst, wherein the improvement comprises carrying out the reaction at a temperature of 90°–130° C. in the presence of an aliphatic hydrocarbon solvent or mixture of such solvents, said solvent boiling in the range of 90°–130° C.

Preferably, n is 1 or 2.
Preferably $R_1$ and $R_2$ are each methyl.
When n is 1, E is preferably alkyl of 1 to 17 carbon atoms.
When n is 2, E is preferably alkylene of 2 to 8 carbon atoms.
Most preferably, n is 2.
Preferably, the reaction is carried out at a temperature of 95°–110° C.

The solvent useful in the instant process is an aliphatic hydrocarbon solvent selected from the group consisting of heptane, isooctane, n-octane, ligroin, mineral spirits and naphtholite with a boiling range of 90°–130° C.

Preferably, the solvent is isooctane or heptane.

The aromatic solvents used in the Russian process such as xylene interact with the N-oxyl radical present to give a variety of by-products such as the N-O-methylbenzyl ether products thus reducing drastically both the yield and purity of the desired N-oxyl compound.

The aliphatic hydrocarbon solvents used in the instant process do not readily react with the N-oxyl radical at the preferred temperature range thus allowing for the N-oxyl product to be isolated in high yield and purity, free of undesired contaminant by-products found with the Russian process. The product is often isolated easily without the need for solvent stripping and recrystallization.

Preferably, in the tetraalkyl orthotitanate or trialkoxy titanium chloride transesterification catalyst, the alkyl or alkoxy is of 1 to 8 carbon atoms.

Preferably, the transesterification catalyst is a tetraalkyl orthotitanate. Most preferably, the catalyst is tetraisopropyl orthotitanate.

The instant invention also pertains to a process for the preparation of compounds of formula III

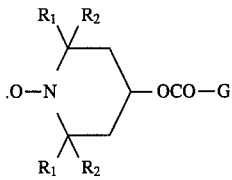

where $R_1$ and $R_2$ are independently methyl or ethyl, or $R_1$ and $R_2$ together are pentamethylene, G is $-E_1-COOT$, $E_1$ is a direct bond, alkylene of 2 to 12 carbon atoms, o-phenylene, m-phenylene or p-phenylene, and T is alkyl of 1 to 4 carbon atoms, by the reaction of essentially one molar equivalent of

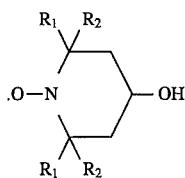

with one molar equivalent of

in the presence of a tetraalkyl orthotitanate or a trialkoxy titanium chloride transesterification catalyst at a reaction temperature of 90°–130° C. in the presence of an aliphatic hydrocarbon solvent or mixture of such solvents, said solvent boiling at 90°–130° C.

Preferably in the compounds of formula III, $R_1$ and $R_2$ are each methyl and $E_1$ is alkylene of 2 to 8 carbon atoms.

The compounds of formula III are also quite effective inhibitors for preventing the premature polymerization of ethylenically unsaturated monomers.

It is also contemplated that the products of the instant process where incomplete transesterification has occurred, that is where some of the alkyl ester groups from the starting material ester $E[COOT]_n$ are still present, are mixtures which are still effective inhibitors for preventing the premature polymerization of ethylenically unsaturated monomers.

The intermediate materials such as the compound of formula II, the various lower alkyl ester starting materials and the titanate catalysts are all items of commerce. The following examples are meant for illustrative purposes only and are not to be construed to limit the scope of the instant invention in any manner whatsoever.

EXAMPLE 1

Bis(1-oxyl-2,2,6,6-tetramethylpiperidin-4-yl) Sebacate

To a 300 ml three-necked flask fitted with a stirrer, nitrogen inlet, thermometer, condenser and Dean-Stark trap is added 34.45 g (0.2 mol) of 1-oxyl-2,2,6,6-tetramethylpiperidin-4-ol, 23.0 g (0.1 mol) of dimethyl sebacate and 110 ml of heptane. The reaction mixture is heated to reflux to dry the contents of the flask and 15 ml of slightly turbid distillate is removed from the Dean-Stark trap. The mixture is cooled to about 75° C. and 0.5 g of tetraisopropyl orthotitanate and 15 ml of heptane is added to the flask. The mixture is heated to reflux and heating at reflux temperature 100°–105° C. is continued for 24 hours with methanol being collected in the Dean-Stark trap. Water (5 ml) is added and heating is continued till all or most of the water is removed. The reaction mixture is allowed to cool slightly, is filtered and washed with heptane. Orange crystals form on standing and are collected by filtration, and washed with heptane. The orange crystalline product melts at 99°–101° C.

Liquid chromatographic assay shows the product to be 97% pure. The recovered yield is 46.8 g (89.6%) while the total yield produced after assaying the residue is 92.3%. Analysis: Calcd for $C_{28}H_{50}N_2O_6$: C, 65.8; H, 9.9; N, 5.5. Found: C, 66.1; H, 10.3; N, 5.4.

EXAMPLE 2

Bis(1-oxyl-2,2,6,6-tetramethylpiperidin-4-yl) Adipate

Following the general procedure of Example 1, 20.8 g (0.119 mol) of 1-oxyl-2,2,6,6-tetramethylpiperidin-4-ol, 10.3 g (0.06 mol) of dimethyl adipate and 70 ml of heptane are heated to reflux and 15 ml of slightly turbid distillate is removed from the Dean-Stark trap. The mixture is cooled to about 75° C. and 0.3 g of tetraisopropyl orthotitanate in 15 ml of heptane is added to the flask. The mixture is heated to reflux and heating at reflux temperature 100°–105° C. is continued for 7 hours. Heating is stopped and the reaction mixture is cooled to room temperature. Another 0.3 g of tetraisopropyl orthotitanate in 15 ml of heptane is added to the flask. The mixture is heated to reflux and heating at reflux temperature 100°–105° C. is again continued for 6 hours. Water (2 ml) and 50 ml of toluene are then added to the reaction mixture and heating is continued till the water is removed. The reaction mixture is then filtered and washed with toluene. The filtrate is vacuum stripped and the residue is recrystallized from heptane. Orange crystals form on standing, are collected by filtration and are washed with heptane. The crystals melt at 121°–122° C.

Liquid chromatographic assay shows the crystals to be 97.7% pure. The recovered yield is 23.6 g (85.1%) and the total yield after assaying the filtrate is 91.2%. Analysis: Calcd for $C_{24}H_{42}N_2O_6$: C, 63.4; H, 9.3; N, 6.2. Found: C, 63.6; H, 9.6; N, 6.1.

EXAMPLE 3

Bis(1-oxyl-2,2,6,6-tetramethylpiperidin-4-yl) Sebacate

Following the procedure of Example 2, 36.2 g (0.21 mol, a 5 mol % excess) of 1-oxyl-2,2,6,6-tetramethylpiperidin-4-ol, 23.0 g (0.1 mol) of dimethyl sebacate and 110 ml of isooctane are reacted to give orange crystals melting at 101°–103° C.

Liquid chromatographic analysis shows the crystals to be 94.1% pure. The recovered yield is 48.9 g (90.0%) and the total yield after assaying the filtrate is 93.0%.

EXAMPLES 4–14

Additional runs are made following the general procedure of Example 1, 2 or 3 to prepare mono- and bis-(1-oxyl-2,2,6,6-tetramethylpiperidin-4-yl) esters. The results are seen in the table below.

| Ex* | Ester | Solvent | Time hrs | Temp. °C. | Percent Total Yield |
|---|---|---|---|---|---|
| 4 | sebacate | heptane | 11 | 100–2 | 91.7 |
| 5 | sebacate | hexane | 14 | 70–71 | low yield due to low temp |
| 6 | sebacate | n-octane | 7 | 126–132 | 82.5 |
| 7 | sebacate | isooctane | 13.5 | 100–2 | 90.0 |
| 8 | succinate | isooctane | 11 | 100–6 | 91.1 |
| 9 | stearate | heptane | 24 | 102–4 | 86.8 |
| 10 | caprylate | heptane | 24 | 101–3 | >95 |
| 11 | caproate | heptane | 24 | 101–3 | >95 |
| 12 | benzoate | heptane | 24 | 101–3 | >95 |
| 13 | oxalate | heptane | 24 | 98–101 | 91.2 |
| 14 | iso-phthalate | heptane | 24 | 98–104 | 93.5 |
| 15 | tere-phthalate | heptane | 24 | 100–102 | 94.0 |

*The catalyst is each of these runs is tetraisopropyl orthotitanate except for Example 9 where the catalyst is tetrabutyl orthotitanate.

Examples 6–8 and 10–13 are run according to the method of Example 1.

Examples 4–5 and 9 are run according to the method of Example 2.

Examples 14–15 are run according to the method of Example 3.

EXAMPLES 16–23

Bis(1-oxyl-2,2,6,6-tetramethylpiperidin-4-yl) Sebacate

When the procedures of Example 1, 2 or 3 are repeated with other tetraalkyl orthotitanate catalysts, the title compound is obtained in excellent yield as seen in the table below.

| Ex | Ti(OR)$_4$ Catalyst R | Solvent | Time hrs | Percent Total Yield* |
|---|---|---|---|---|
| 16 | ethyl | heptane | 24 | 93.5 |
| 17 | propyl | heptane | 24 | 87.2 |
| 18 | butyl | heptane | 13 | 80.7 |
| 19 | ethyl | heptane | 24 | 87.5 |
| 20 | isopropyl | isooctane | 13 | 93.0 |
| 21 | isopropyl | heptane | 24 | 92.3 |
| 22 | 2-ethyl-hexyl | heptane | 24 | 89.2 |
| 23 | ** | heptane | 24 | 89.1 |

*Total yield is determined after LC-assay of the filtrate from the experiment.
**Catalyst is triisopropoxy titanium chloride.

EXAMPLE 24

1-Oxyl-2,2,6,6-tetramethylpiperidin-4-yl Ethyl Sebacate

When following the procedure of Example 1, equimolar amounts of 1-oxyl-2,2,6,6-tetramethylpiperidin-4-ol and diethyl sebacate are reacted in heptane in the presence of tetraisopropyl orthotitanate, the title compound is prepared.

EXAMPLE 25

1-Oxyl-2,2,6,6-tetramethylpiperidin-4-yl Methyl Sebacate
Bis(1-oxyl-2,2,6,6-tetramethylpiperidin-4-yl) Sebacate When following the procedure of Example 1, the transesterification reaction is stopped after 4 hours before the transesterification is complete. The reaction mixture contains a mixture of materials including some of both title compounds. The mixture can be separated into its individual components. The 1-oxyl-2,2,6,6-tetramethylpiperidin-4-yl methyl sebacate component is isolated and identified as seen by the elemental analysis below. Analysis: Calcd for $C_{20}H_{36}NO_5$: C, 64.8; H, 9.8; N, 3.8. Found: C, 65.1; H, 10.2; N, 3.8.

EXAMPLE 26–32

Following the general method of Example 24, the following esters of formula III are prepared.

| Ex | Ester |
|---|---|
| 26 | 1-oxyl-2,2,6,6-tetramethylpiperidin-4-yl ethyl oxalate |
| 27 | 1-oxyl-2,2,6,6-tetramethylpiperidin-4-yl ethyl succinate |
| 28 | 1-oxyl-2,2,6,6-tetramethylpiperidin-4-yl ethyl glutarate |
| 29* | 1-oxyl-2,2,6,6-tetramethylpiperidin-4-yl methyl adipate |
| 30 | 1-oxyl-2,2,6,6-tetramethylpiperidin-4-yl methyl suberate |
| 31 | 1-oxyl-2,2,6,6-tetramethylpiperidin-4-yl ethyl phthalate |
| 32 | 1-oxyl-2,2,6,6-tetramethylpiperidin-4-yl methyl isophthalate |

*Analysis:
Calcd for $C_{16}H_{28}NO_5$: C, 61.1; H, 9.0; N, 4.5.
Found: C, 61.1; H, 9.2; N, 4.5.

EXAMPLE 33

1-Oxyl-2,2,6,6-tetramethylpiperidin-4-yl Ethyl Sebacate

When following the procedure of Example 24, the tetraalkyl orthotitanate transesterification catalyst is replaced by an equivalent amount of triisopropoxy titanium chloride transesterification catalyst, the title compound is made in excellent yield.

What is claimed is:

1. An improved process for the preparation of an N-oxyl compound of formula I

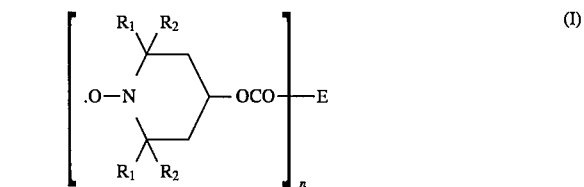

wherein n is 1, 2, 3 or 4, $R_1$ and $R_2$ are independently methyl or ethyl, or $R_1$ and $R_2$ together are pentamethylene, when n is 1, E is alkyl of 1 to 19 carbon atoms, alkenyl of 2 to 17 carbon atoms, phenyl or said phenyl substituted by 1 to 3 alkyl of 1 to 4 carbon atoms, when n is 2, E is a direct bond, alkylene of 2 to 12 carbon atoms, o-phenylene, m-phenylene or p-phenylene, when n is 3, E is alkanetriyl of 3 to 7 carbon atoms, 1,2,4-benzenetriyl or 1,3,5-benzenetriyl, and when n is 4, E is alkanetetrayl of 4 to 8 carbon atoms or 1,2,4-benzenetriyl or 1,3,5-benzenetriyl, by the reaction of essentially n equivalents of

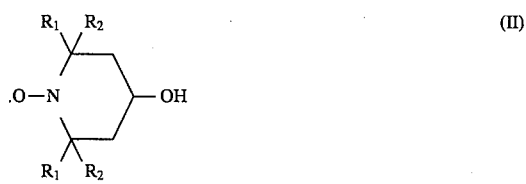

with one equivalent of

E-[COOT]$_n$ where T is alkyl of 1 to 4 carbon atoms, and $R_1$, $R_2$ n and E are as described above, in the presence of a tetraalkyl orthotitanate or a trialkoxy titanium chloride transesterification catalyst, wherein the improvement comprises carrying out the reaction at a temperature of 90°–130° C. in the presence of an aliphatic hydrocarbon solvent or mixture of such solvents, said solvent boiling in the range of 90°–130° C.

2. A process according to claim 1 where in formula I, n is 1 or 2.

3. A process according to claim 1 where in formula I, $R_1$ and $R_2$ are each methyl.

4. A process according to claim 1 where in formula I, when n is 1, E is alkyl of 1 to 17 carbon atoms.

5. A process according to claim 1 where in formula I, when n is 2, E is alkylene of 2 to 8 carbon atoms.

6. A process according to claim 1 where in formula I, n is 2.

7. A process according to claim 1 wherein the reaction is carried out at a temperature of 95°–110° C.

8. A process according to claim 1 wherein the solvent is an aliphatic hydrocarbon solvent selected from the group consisting of heptane, isooctane, n-octane, ligroin, mineral spirits and naphtholite with a boiling range of 90°–130° C.

9. A process according to claim 1 wherein the solvent is isooctane or heptane.

10. A process according to claim 1 where in the tetraalkyl orthotitanate or trialkoxy titanium chloride transesterification catalyst, alkyl or alkoxy is of 1 to 8 carbon atoms.

11. A process according to claim 1 where the catalyst is a tetraalkyl orthotitanate.

12. A process according to claim 11 wherein the catalyst is tetraisopropyl orthotitanate.

13. A process according to claim 1 wherein the compound of formula I is bis(1-oxyl-2,2,6,6-tetramethylpiperidin-4-yl) sebacate, bis(1-oxyl-2,2,6,6-tetramethylpiperidin-4-yl) adipate, bis(1-oxyl-2,2,6,6-tetramethylpiperidin-4-yl) succinate, bis(1-oxyl-2,2,6,6-tetramethylpiperidin-4-yl) oxalate, bis(1-oxyl-2,2,6,6-tetramethylpiperidin-4-yl) isophthalate, bis(1-oxyl-2,2,6,6-tetramethylpiperidin-4-yl) terephthalate, 1-oxyl-2,2,6,6-tetramethylpiperidin-4-yl benzoate, 1-oxyl-2,2,6,6-tetramethylpiperidin-4-yl stearate, 1-oxyl-2,2,6,6-tetramethylpiperidin-4-yl caproate or 1-oxyl-2,2,6,6-tetramethylpiperidin-4-yl caprylate.

14. A process according to claim 13 wherein the compound of formula I is bis(1-oxyl-2,2,6,6-tetramethylpiperidin-4-yl) sebacate.

15. A process for the preparation of a compound of formula III

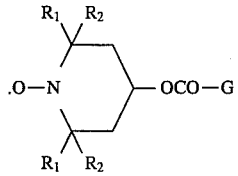
(III)

where $R_1$ and $R_2$ are independently methyl or ethyl, or $R_1$ and $R_2$ together are pentamethylene, G is $-E_1-COOT$, $E_1$ is a direct bond, alkylene of 2 to 12 carbon atoms, o-phenylene, m-phenylene or p-phenylene, and T is alkyl of 1 to 4 carbon atoms, by the reaction of essentially one molar equivalent of

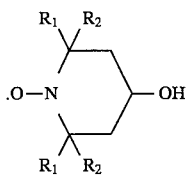
(II)

with one molar equivalent of $E_1-[COOT]_2$ in the presence of a tetraalkyl orthotitanate or a trialkoxy titanium chloride transesterification catalyst at a reaction temperature of 90°–130° C. in the presence of an aliphatic hydrocarbon solvent or mixture of such solvents, said solvent boiling at 90°–130° C.

16. A process according to claim 15 where in the compounds of formula III, $R_1$ and $R_2$ are each methyl and E is alkylene of 2 to 8 carbon atoms.

17. A process according to claim 15 wherein the reaction is carried out at a temperature of 95°–110° C.

18. A process according to claim 15 wherein the solvent is an aliphatic hydrocarbon solvent selected from the group consisting of heptane, isooctane, n-octane, ligroin, mineral spirits and naphtholite with a boiling range of 90°–130° C.

19. A process according to claim 15 wherein the solvent is isooctane or heptane.

20. A process according to claim 15 where in the tetraalkyl orthotitanate or trialkoxy titanium chloride transesterification catalyst, alkyl or alkoxy is of 1 to 8 carbon atoms.

21. A process according to claim 15 where the catalyst is a tetraalkyl orthotitanate.

22. A process according to claim 21 wherein the catalyst is tetraisopropyl orthotitanate.

23. A process according to claim 15 wherein the compound of formula III is 1-oxyl-2,2,6,6-tetramethylpiperidin-4-yl ethyl oxalate 1-oxyl-2,2,6,6-tetramethylpiperidin-4-yl ethyl succinate 1-oxyl-2,2,6,6-tetramethylpiperidin-4-yl ethyl glutarate 1-oxyl-2,2,6,6-tetramethylpiperidin-4-yl methyl adipate 1-oxyl-2,2,6,6-tetramethylpiperidin-4-yl methyl suberate 1-oxyl-2,2,6,6-tetramethylpiperidin-4-yl ethyl sebacate, 1-oxyl-2,2,6,6-tetramethylpiperidin-4-yl methyl sebacate, 1-oxyl-2,2,6,6-tetramethylpiperidin-4-yl ethyl phthalate or 1-oxyl-2,2,6,6-tetramethylpiperidin-4-yl methyl isophthalate.

* * * * *